United States Patent [19]

Denton et al.

[11] Patent Number: 4,911,921

[45] Date of Patent: Mar. 27, 1990

[54] HIGH IBUPROFEN CONTENT GRANULATIONS

[75] Inventors: Larry E. Denton, Collinsville, Ill.; Anil M. Salepkar, St. Louis, Mo.

[73] Assignee: Mallinckrodt, Inc., St. Louis, Mo.

[21] Appl. No.: 306,014

[22] Filed: Feb. 2, 1989

[51] Int. Cl.[4] .................... A61K 31/74; A61K 31/79; A61K 9/26; A61K 9/36
[52] U.S. Cl. ........................................ 424/80; 424/78; 424/482; 424/479; 424/480; 424/470; 514/570
[58] Field of Search ................. 424/80, 78, 482, 479, 424/480, 470; 514/570

[56] References Cited

U.S. PATENT DOCUMENTS

| | | | |
|---|---|---|---|
| 3,108,046 | 10/1963 | Harbit | 514/165 |
| 4,209,513 | 6/1980 | Torode et al. | 424/228 |
| 4,609,675 | 9/1986 | Franz | 514/568 |
| 4,661,521 | 4/1987 | Salpekar et al. | 514/613 |
| 4,753,801 | 6/1988 | Oren et al. | 424/80 |
| 4,757,090 | 7/1988 | Salepkar et al. | 514/613 |
| 4,806,359 | 2/1989 | Radebaugh et al. | 424/470 |

FOREIGN PATENT DOCUMENTS 0172014 2/1986 European Pat. Off. ............ 514/570

OTHER PUBLICATIONS

GAF Corp. "Tableting with Plasdone® Povidone USP" 1981.

Primary Examiner—Joseph L. Schofer
Assistant Examiner—Carmen Pili-Curtis
Attorney, Agent, or Firm—Grace L. Bonner; Roy J. Klostermann

[57] ABSTRACT

A granular pharmaceutical composition containing 85 to 99 percent ibuprofen, 0.9 to 15.0 percent binder, and 0.1 to 5.0 percent polyvinylpyrrolidone, wherein the polyvinylpyrrolidone forms a film with a portion of said binder to form agglomerates, is disclosed. Ibuprofen may be fluidized with a portion of the binder in a fluid bed apparatus and sprayed with an aqueous dispersion of polyvinylpyrrolidone and the remainder of the binder. This granulation may be subsequently blended with additional excipients and, optionally, additional active pharmaceutical ingredients for direct compression into tablets.

8 Claims, No Drawings

HIGH IBUPROFEN CONTENT GRANULATIONS

FIELD OF THE INVENTION

The present invention relates to pharmaceutical ibuprofen compositions and wet granulation methods of preparing them. More particularly, the invention relates to new granular compositions containing high levels of ibuprofen which are eminently suitable for subsequent blending with lubricants, binders, disintegrants, and, optionally, additional pharmaceutical active ingredients, for tabletization.

BACKGROUND OF THE INVENTION

Ibuprofen, the generic name for 2-(4-isobutylphenyl)-propionic acid, is a well known anti-inflammatory drug and is disclosed in U.S. Pat. Nos. 3,228,831 and 3,385,886. Normally, ibuprofen is formulated for sale to the consumer in the form of compressed tablets or capsules.

Previously known compositions produced by a wet granulation method have required relatively large percentages of excipients to produce a compressible formulation. This lowers the maximum level of ibuprofen that can be contained in the formulation. This in turn increases the size of the tablet formed from such a formulation, especially a problem for the higher dose level tablets, such as 800 or 1200 mg units. This increased size is undesirable both from a manufacturing and handling standpoint and a patient acceptability standpoint. There has been a need, therefore, for higher active ingredient levels in compressible formulations.

U.S. Pat. No. 4,609,675 discloses a method of preparing a pharmaceutical ibuprofen-containing granulate composition suitable for preparing tablets of relatively high dosage. This is accomplished by dry mixing ibuprofen with 1 to 15 percent by weight croscarmellose sodium NF (cross-linked sodium carboxymethylcellulose). This dry granulation method meets this need described above, but uses a relatively expensive additive to accomplish it. Croscarmellose sodium NF is used at levels up to 15 percent, preferably about 7 to 8 percent. This contributes significantly to the cost of the formulation.

It is an object of the present invention to provide an ibuprofen granulation formulation having a high level of active ingredient and which can be ultimately tabletized by direct compression.

It is a further object of the present invention to provide an ibuprofen granulation that can be formulated with additional excipients, and, optionally other active ingredients, and compressed into tablets having high hardness, short disintegration time, and fast dissolution rate without being unacceptably friable.

It is a still further object of the invention to provide a wet granulation method that produces a granulation formulation having a high ibuprofen content.

DESCRIPTION OF THE INVENTION

Generally stated, the present invention provides a free-flowing, high-ibuprofen content granulation capable of being blended with external excipients to produce a formulation capable of being directly formed into a tablet having high hardness, short disintegration time and short dissolution time. This granulation has as components (a) ibuprofen in an amount of about 85 percent or more on a dry weight basis, (b) a pharmaceutically acceptable binder in a binding amount, (c) polyvinylpyrrolidone (PVP) in a film-forming amount, and (d) moisture up to 2.0 percent of the total weight. This granulation is in the form of agglomerates of ibuprofen and dry binder held together in some manner by the binder and PVP.

Formulations of this granuation are capable of being used in a wide variety of dosage forms such as compressed tablets and dosage sizes ranging from 100 to 1200 mg per unit, and may contain other active ingredients. They are particularly suited for preparing tablets having 800 or more mg ibuprofen per unit.

In another aspect, this invention provides for a method of preparing the granulation just described by a wet granulation method, i.e., fluid bed granulation. The method follows the steps of (a) charging the ibuprofen and a portion of the binder to a fluid bed granulator-dryer, (b) fluidizing the ibuprofen and binder until thoroughly blended, (c) dispersing the remaining binder and the PVP in water using a high shear mixer to form a slurry having from about 5 to 10 percent by weight solids, (d) spraying the binder/PVP dispersion onto the fluidized bed of ibuprofen and binder at a rate sufficient to maintain the powder bed moisture between about 5 and about 20 percent by weight, (e) continuing drying until the moisture level of the bed is 2.0 percent or less, and (f) optionally, sizing the material to the desired particle size distribution.

DETAILED DESCRIPTION OF THE INVENTION AND THE MANNER AND PROCESS OF MAKING AND USING IT

The binder used in the present granulation can be selected from those known in the art to be suitable for use in directly compressible pharmaceutical formulations. Examples of these are starches, celluloses, and sugars. More specifically the binder may be pregelatinized starch, microcrystalline cellulose, lactose, or corn starch. Pregelatinized starch NF is preferred.

Polyvinylpyrrolidone, also known as povidone or PVP, is available in various forms from various suppliers. A wide range of molecular weights are available. The higher molecular weight products, 600,000 Daltons and above (K values of 90 or greater), are preferred for the present invention because eutectic formation during storage at elevated temperatures can be a problem with ibuprofen-PVP formulations. Higher molecular weight PVP products minimize this undesirable property. Particular commercial products that be used in the present invention are Plasdone ® K-90 and K-120 (Povidone U.S.P.) from GAF Corporation.

Ibuprofen and dry binder are powdery materials, which by themselves do not form satisfactory tablets by direct compression. The PVP-binder mixture or dispersion works in the presence of water to form a film that agglomerates these powdery materials to form granules. These granules are more free-flowing than the powders one starts with and their compressibility is greatly enhanced. PVP is used in a film-forming amount. This amount is generally from about 0.1 to about 5.0 percent of the granulation on a dry weight basis.

The binder component, in addition to its binding properties during agglomeration or granulation, is also an aid to the disintegration and dissolution of tablets made with the present granulation. The balance between good compression properties and good disintegration properties is achieved by using a portion of the binder in a dry form and a portion in a wetted form, the latter working with PVP for film formation and agglomeration.

Thus, the binder component of the present granulation serves to impart good binding and disintegrant properties as well as a good balance thereof to the final dosage forms prepared from the granulation, i.e., tablets. It is included in an amount effective for imparting to the granulation and formulations made therefrom, the capability of being formed into tablets having high hardness (e.g., about 8 kp or more), short disintegration time (e.g., about 10 minutes or less), and short dissolution time (e.g., about 20 minutes or less for 80 percent or more ibuprofen to dissolve). In general, such effective amount of total binder in the granulation is from about 0.9 percent to about 15 percent on a dry weight basis, preferably, from about 5.0 to about 10.0 percent, and more preferably, about 9.5 percent. In general, about half, or more preferably, slightly less than half, of the amount of binder is used in a dry form to aid in dissolution and disintegration. The remainder, preferably slightly more than half of the total amount is used in a wetted form with PVP to bind the agglomerates, impart compressibility and enhance tablet hardness.

A preferred embodiment includes the following components in the amounts indicated with a moisture content of 0.8 to 1.8 percent of the total weight:

|  | Percent (dry wt.) |
|---|---|
| Ibuprofen | 90.0 |
| Pregelatinized Starch NF | 9.5 |
| PVP | 0.5 |

The granulation of this invention is preferably made by the method mentioned above, which includes the use of a fluid bed granulator-dryer. A suitable sized fluid bed granulator-dryer (FBGD) is charged with the ibuprofen and a portion of the binder. The amount of binder added from about 0.5 to about 8 percent by weight based on the total dry weight of the granulation. Preferably, about 4.5 percent on the above basis is charged to the fluid bed. The materials are fluidized until thoroughly blended. The remaining binder, i.e., about 0.5 to about 7 percent, which was not added to the fluid bed is dispersed with the PVP in water to yield a slurry of between about 5 and about 10 weight percent solids, using a high shear mixer. Preferably, about 5 percent binder is dispersed. The dispersion is then sprayed onto the fluidized bed of ibuprofen/binder at a rate sufficient to maintain the powder bed moisture between about 5 and about 20 weight percent, and preferably between about 7 and about 14 weight percent. After complete addition of the dispersion to the fluid bed, the fluidization is continued until the bed moisture is reduced to less than 2.0 weight percent, and preferably from about 0.8 to about 1.8 weight percent. The fluidization is then terminated.

The fluid bed granulator-dryer is operated under the following conditions: a stream of heated air is introduced from the bottom of the fluid bed at a sufficient velocity to fluidize the powder bed and at a temperature sufficient to heat the powder bed at between about 20° C. to about 50° C. The optimum air velocity, inlet air temperature and the powder bed temperature are dependent on the batch size, dew point of air, and spray rate of the binder solution during the granulation phase and therefore are adjusted accordingly. The particle size of the bed material is influenced by the atomization pressure used to spray the granulating liquid as well as by the moisture level of the fluid bed during the granulation phase. By adjusting operative parameters, the desired particle size distribution for the granulation can be obtained. A further sizing of the dry granulation (to obtain a narrow particle size distribution) may be achieved using a Glatt Quick Sieve or other suitable sizing equipment. A preferred particle size distribution is 100 percent from 20 to 200 mesh.

The granulation thus produced could be directly compressed to form tablets. However, better tablets are produced by blending the granulation by known methods, such as using a double cone blender, with additional excipients that aid in the compression and provide improved properties such as hardness and disintegration time. These excipients may be selected from the whole range known in the art and are chosen based on the desired properties of the tablet produced.

It is highly desirable to add a lubricant that aids in the production of the tablets. Examples of such lubricants are stearic acid, metal stearates, sodium lauryl sulfate, polyethylene glycol, hydrogenated vegetable oils and talc. Silicon dioxide can also be added to impart better mold release properties.

Additionally, further tablet-binding agents in tablet-binding amounts can be added. Materials suitable for use as the optionally included additional binder agent include, for example, starch (starch paste), polyvinylpyrrolidone, hydroxypropylmethylcellulose, hydroxypropylcellulose, gelatin, natural gums (e.g., gum acacia, gum tragacanth, etc.), lactose, sucrose, mannitol, ethylcellulose, microcrystalline cellulose, synthetic polymer binders commonly used in the industry, and compatible mixtures of two or more such materials.

Disintegrants, such as cross-linked polyvinylpyrrolidone (crospovidone) or sodium starch glycolate, may also be added in disintegrating amounts. Additional water may be added to facilitate compression.

The amounts of the added excipients are preferably the minimum amounts necessary to accomplish their purposes. The lubricant component is present in a lubricating amount sufficient to impart mold release properties to tablets formed from the formulation and preferably insufficient to increase disintegration time and dissolution time of such tablets, and preferably insufficient to decrease the hardness obtainable for tablets formed from a formulation having no additional lubricant. A preferred composition for tabletting, prepared using the preferred embodiment of the granulation as stated above, is shown in Table 1.

TABLE 1

| TABLET FORMULATION | |
|---|---|
| MATERIAL | % |
| 90% IBUPROFEN GRANULATION | 79.3 |
| CALCIUM STEARATE | 0.8 |
| STEARIC ACID | 2.4 |
| SILICON DIOXIDE | 0.5 |
| SODIUM STARCH GLYCOLATE | 4.0 |
| MICROCRYSTALLINE CELLULOSE | 6.5 |
| LACTOSE | 6.5 |

The granulation of the present invention is also particularly useful in producing combination pharmaceuticals. The high ibuprofen content and limited number of excipients make it amenable to blending with other active ingredients. Examples of such active ingredients are antihistimines, decongestants, antitussives, and other analgesics, muscle relaxants, and the like.

Tablets prepared from the present granulation formulations can contain from 100 to 1200 mg ibuprofen. The formulations are particularly helpful in preparing tablets containing high doses of ibuprofen such as 400 mg or more per tablet.

As used herein the term "KP" means kilo ponds, as well known unit of force for expressing hardness or crushing strength of pharmaceutical tablets, when such hardness is determined on a Schleuniger Tablet Hardness Tester.

The following examples and tables illustrate the invention. As used herein, the following terms have the meanings indicated:

(a) "Disintegration time" means the time measured using the disintegration time test method set forth in U.S. Pharmacopeia (hereinafter "USP") XXI for uncoated tablets except that the disks are not employed;

(b) "Dissolution time" means the time measured using the dissolution time test method set forth in USP XXI for ibuprofen tablets;

(c) "Hardness" means the hardness measured on a Schleuniger Tablet Hardness Tester;

(d) "Friability" means the friability measured on a Roche Friabulator for 40 tablets and 375 revolutions.

Unless otherwise indicated, all tablet hardness values are averages for 10 tablets and all tablet weights are averages obtained by weighing 20 tablets as a whole and then dividing by 20. Further, unless otherwise indicated, tablet disintegration times were measured for tablets having about 9 kp hardness.

EXAMPLE 1

Ninety percent ibuprofen granulation

A granulation composition having the following dry weight composition was prepared in a fluid bed granulator-dryer (Aeromatic, Inc., Model STREA-1):

|  | Percent (dry wt.) |
|---|---|
| Ibuprofen | 90.0 |
| Pregelatinized Starch NF | 9.5 |
| Plasdone ® K-90, PVP U.S.P. | 0.5 |

The starch was split into two parts as described above. The first part, 4.4 percent of total solids, was fluidized with the ibuprofen in the granulator. The second part, 5.1 percent of total solids, was dispersed in warm water with the PVP.

The batch size exclusive of water was 1.0 kg. After spraying, the granulation was dried to a moisture level of less than 2.0 percent of the total weight of the granulation.

EXAMPLE 2

200 and 800 mg ibuprofen tablets

Ninety percent ibuprofen granulation, prepared as in Example 1, was formulated as shown in Table 1, above, to produce a directly compressible formulation.

Tablets having an average of 200 or 800 mg ibuprofen per unit were formed. They had the physical properties shown in Table 2.

TABLE 2

| TEST | TABLET PROPERTIES | |
|---|---|---|
|  | 200 MG. | 800 MG. |
| Hardness (kp) | 10.2 | 19.2 |
| Thickness (inch) | 0.206 | 0.339 |
| Friability (%) | 0.22 | 0.20 |
| Disintegration Time (minutes:seconds) | 6:30 | 6:30 |
| Dissolution (by USP XXI, Method 2) (% in 30 minutes) | 100 | 97.4 |

What is claimed is:

1. A pharmaceutical, high drug content ibuprofen granulation composition, comprising
   (a) about 85 to about 99 percent ibuprofen on a dry weight basis;
   (b) about 0.9 to about 15.0 percent pharmaceutically acceptable binder on a dry weight basis;
   (c) about 0.1 to 5.0 percent polyvinylpyrrolidone on a dry weight basis; and
   (d) a moisture content of 0.1 to 2.0 percent of the total weight;

said granulation being in the form of agglomerates of ibuprofen and binder held together by binder and polyvinylpyrrolidone.

2. A composition according to claim 1, wherein said binder is selected from a group consisting of starches, celluloses, and sugars.

3. A composition according to claim 2, wherein said binder is pregelatinized starch.

4. A composition according to claim 2, wherein said binder is microcrystalline cellulose.

5. A composition according to claim 1, wherein said polyvinylpyrrolidone has a molecular weight average greater than 600,000 Daltons (a K value of 90 or greater).

6. A composition according to claim 1, wherein said moisture is from about 0.8 to about 1.8 percent by total weight.

7. A composition according to claim 1, wherein said polyvinylpyrrolidone is about 0.5 percent on a dry weight basis.

8. A composition according to claim 1, wherein said ibuprofen is present at about 90 percent on a dry weight basis; said binder is present at about 9.5 percent on a dry weight basis; and said polyvinylpyrrolidone is present at about 0.5 percent on a dry weight basis.

* * * * *